United States Patent [19]

Yannopoulos et al.

[11] 4,397,888
[45] Aug. 9, 1983

[54] THICK FILM SENSOR FOR HYDROGEN AND CARBON MONOXIDE

[75] Inventors: Lymperios N. Yannopoulos, Churchill Boro.; Chikara Hirayama, Franklin Township, both of Pa.

[73] Assignee: Westinghouse Electric Corp., Pittsburgh, Pa.

[21] Appl. No.: 356,683

[22] Filed: Mar. 10, 1982

Related U.S. Application Data

[62] Division of Ser. No. 224,873, Jan. 14, 1981, abandoned.

[51] Int. Cl.³ .............................................. B05D 5/12
[52] U.S. Cl. ..................................... 427/86; 427/125; 427/126.3; 427/376.3; 427/376.6; 324/71.5; 340/633; 340/634; 422/94
[58] Field of Search .................. 324/71 SN; 340/633, 340/634; 422/94; 427/86, 125, 126.3, 376.3, 376.6, 383.3

[56] References Cited

U.S. PATENT DOCUMENTS

| 4,030,340 | 6/1977 | Cheng | 422/98 |
| 4,045,178 | 8/1977 | Okinaka et al. | 422/98 |
| 4,241,019 | 12/1980 | Nakatani et al. | 422/98 |
| 4,242,303 | 12/1980 | Takahashi | 422/98 |
| 4,242,303 | 12/1980 | Kitamura | 422/98 |

FOREIGN PATENT DOCUMENTS 54-104397  8/1979  Japan ..................................... 422/98

Primary Examiner—Michael R. Lusignan
Assistant Examiner—Richard Bueker
Attorney, Agent, or Firm—M. P. Lynch

[57] ABSTRACT

An improved thick film stannic oxide sensor is disclosed whereby the sensitivity of the sensor to CO is enhanced by the addition of a rare earth oxide to the sensor composition and the catalytic reactivity of the sensor, when contacted by a gas containing a reducing constituent, i.e., $H_2$ or CO, and oxygen, is enhanced by employing $RuCl_3$ or $PtCl_2$ as a catalyst.

4 Claims, 6 Drawing Figures

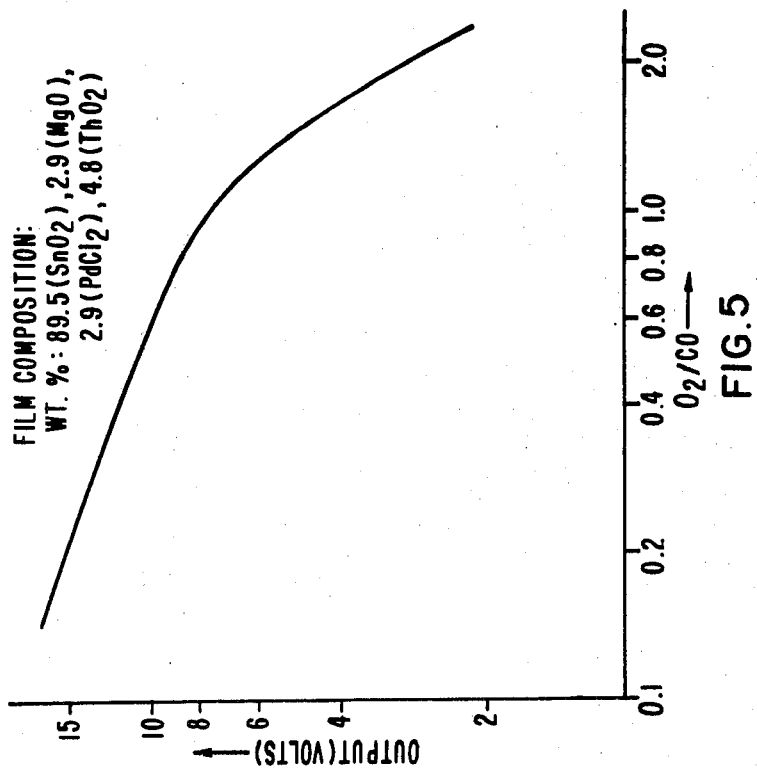
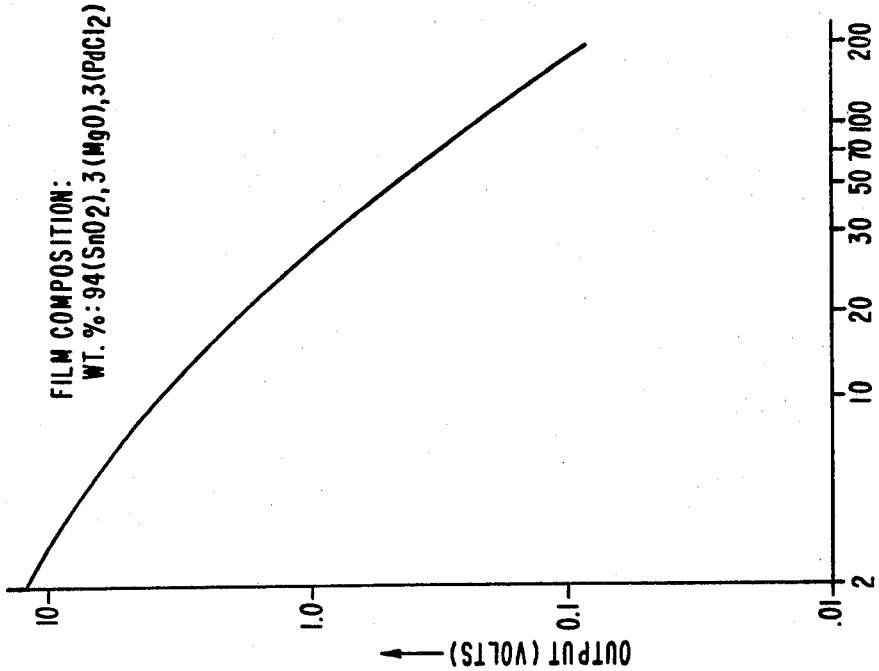

THICK FILM SENSOR FOR HYDROGEN AND CARBON MONOXIDE

This is a division of application Ser. No. 224,873, filed Jan. 14, 1981, now abandoned.

BACKGROUND OF THE INVENTION

The selective detection of CO and $H_2$ gas constituents by a stannic oxide ($SnO_2$) element has been the topic of technical papers and publications. The stannic oxide element corresponds to an n-type semiconductor oxide which exhibits changes in electrical resistivity on exposure to gases such as $H_2$ and CO. This oxide responds primarily to $H_2$ in the temperature range of 200°–250° C. when it is intimately mixed with small amounts of sintering agent such as MgO and a catalyst such as $PdCl_2$. When small amounts of $ThO_2$ are added to the above oxide the surface activity is shifted towards CO gas. To the latter formulation, the incorporation of small amounts of hydrophobic $SiO_2$ to remove water from contact with the stannic oxide enhances the sensitivity of the element to CO.

Publications describing thick film sensors, which are incorporated herein by reference include:

(1) Thick-Film CO Gas Sensors, by Nitta et al., appearing in IEEE Transactions on Electron Devices, March, 1979;

(2) CO Gas Detection By $ThO_2$—Doped $SnO_2$, by Nitta et al., appearing in Journal of Electronic Materials, Vol. 8, No. 5, 1979.

SUMMARY OF THE INVENTION

Although electrical resistivity changes which are detected in semiconductor oxides occur inside the surface of the semiconductor, they are induced by the electric charge of the surface. This charge resides in surface states or in additional allowed energy levels. These energy levels arise as a result of several causes including the adsorption of foreign atoms or molecules. If these surface adsorbed atoms or molecules are catalyzed to react with a gas or a mixture of gases and removed from the surface, then, a change in the resistivity of the semiconductor oxide is detectable. The magnitude of this change is a function of the concentration of the removed surface adsorbed atoms or molecules and, thus is a function of the catalytically active gas. Under certain conditions, these catalytic surface reactions selectively involve only one reducing gas component in a mixture of gases. This selectivity is achieved by appropriate additives to the semiconductor oxide.

It has been determined experimentally that the substitution of a rare earth oxide, such as lanthanum oxide, which exhibits a greater hydrophobic effect than thorium oxide, for the thorium oxide in the published stannic oxide gas sensor will render the stannic oxide gas sensor more sensitive to CO.

Further, the process of fabricating a thick film semiconductor sensor for $H_2$ and CO has been improved by adding the catalyst to a stannic oxide solution to assure optimum distribution of the catalyst in the matrix of the final semiconductor film sensor. While the prior art discusses the use of palladium chloride ($PdCl_2$) as the catalyst, it has been determined experimentally that the use of $RuCl_3$ and $PtCl_2$ in amount of between 1 and 5 mole percent enhances the catalytic action of the semiconductor oxide sensor thus increasing the sensitivity of the sensor.

While the stannic oxide sensor provides gas constituent monitoring in temperatures of between approximately 200° and 250° C. the application of the stannic oxide sensor in higher temperature environments, as would be encountered in various combustion processes, would result in the stannic oxide assuming the characteristics of an insulator. It has been determined experimentally that an indium oxide ($In_2O_3$) sensor doped with tin (Sn) in a range of about 2–5 mole percent exhibits good electronic conductivity characteristics and operational stability at temperatures in excess of 250° C. Thus, this new semiconductor oxide composition permits fabrication of effective thick film sensors for CO and $H_2$ in high temperature environments.

DESCRIPTION OF THE DRAWING

The invention will become more readily apparent from the following exemplary description in connection with the accompanying drawing:

FIGS. 3, 4 and 5 are graphic illustrations of the operation of devices formulated in accordance with the embodiment of FIG. 2.

DESCRIPTION OF THE PREFERRED EMBODIMENT

Figure 1:
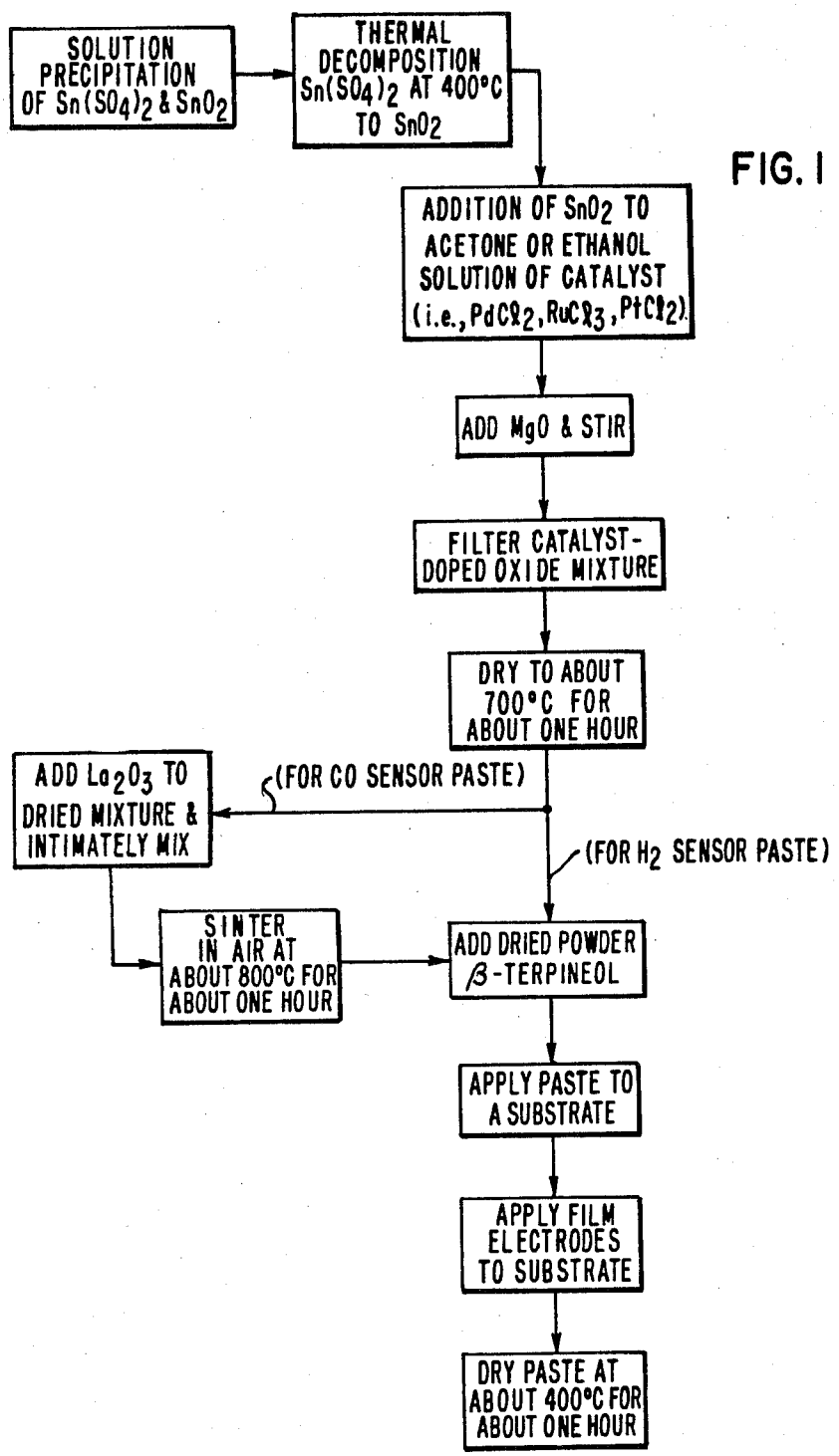
FIG. 1 is a diagram of the process steps for fabricating the improved semiconductor thick film sensor.
Figure 2A:
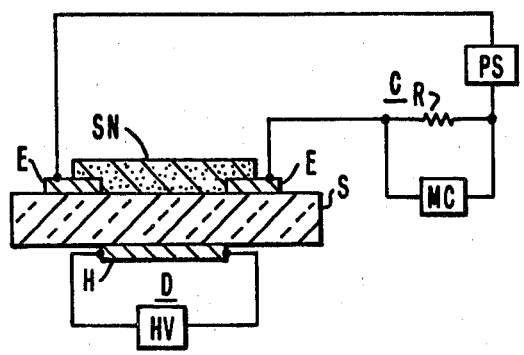
FIG. 2 is a schematic illustration of an embodiment of the invention.
Figure 2B:
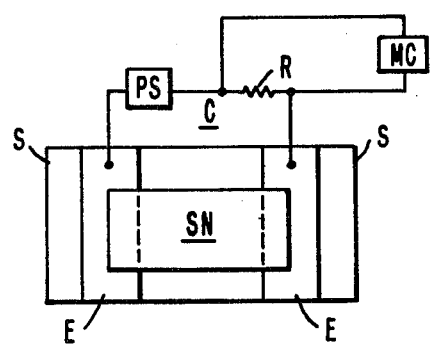

The improved stannic oxide sensor SN, fabricated in accordance with the process steps of FIG. 1 and typically illustrated in a gas sensing device D in FIG. 2, is realized as a result of a preparation procedure whereby the stannic oxide sensor is developed as a paste through solution processing steps wherein a uniform distribution of the catalyst is achieved by a colloidal suspension during the preparation of the stannic oxide ($SnO_2$) paste.

The physical characteristics of the stannic oxide sensor SN are determined in the preparation process of FIG. 1.

In the application of the stannic oxide film as a gas sensor SN to monitor CO and $H_2$, an oxide power with high surface area is required in order to optimize the efficiency of the gas-surface catalyzed reaction. This condition is achieved in the disclosed gas sensor SN as a result of the formation of stannic oxide by heating the precipitate formed using a precipitation method from a sulfate homogeneous solution. This technique yields a fine precipitate of a mixture of stannic oxide and sulfate. When the sulfate portion is heated to about 400° C. it also produces stannic oxide.

The above precipitation is accomplished by the slow hydrolysis of the urea $H_2N$—CO—$NH_2$. This slow hydrolysis permits an initial slow rise of the pH of the solution and controls both the rate and the size of the precipitate.

It has been determined experimentally that 0.25 grams of tin (Sn) is precipitated as basic stannic sulfate by heating to a boiling condition a solution of 50 grams of urea, 50 milliliters of sulfuric acid ($H_2SO_4$), 2 grams of ammonium sulfate [$(NH_4)_2SO_4$], and sufficient hydrochloric acid (HCl) to furnish an initial pH of 0.50. This solution was contained in a 400 ml volume. The solution is rapidly heated to boiling and then transferred to an air bath heater designed to heat most of the liquid portion. The solution is then boiled for about 2½ hours while taking precautions to minimize bumping and maintaining the liquid level through the addition of distilled water. The pH of the precipitate resulting from this process is approximately 1.3.

It has been further determined in developing a gas sensor SN from the stannic oxide material that a uniform distribution of the catalyst within the stannic oxide film significantly enhances the sensitivity of the film thus making it a valid candidate for a gas sensor device. The catalyst, which is typically a noble or precious metal, is distributed in the above-processed stannic oxide precipitate, or powder, via solution deposition. The small amounts of the catalyst material required, i.e., 1–5 wt.%, is incorporated by immersing the prepared stannic oxide powder in an acetone or ethanol solution of the precious metal chloride, i.e., $PdCl_2PtCl_2$, or $RuCl_3$. It has been determined experimentally that the immersion technique provides good adherence of the catalyst on the surface of the stannic oxide powder. This enhances the resistivity changes in thick films thus rendering the films suitable as a gas sensing device D when connected with appropriate circuitry as illustrated in FIG. 2. The resulting instrument combination provides practical measurements of designated gas constituents. The use of a sintering agent MgO, as disclosed in the prior art, can be employed in developing the gas sensor SN by adding the sintering agent in combination with the catalyst as described above.

The sintering agent is mixed with the catalyst-containing stannic oxide powder. After drying in air at 700° C. for about one hour the above stannic oxide powder mixture material is processed to form a paste of the proper porosity to optimize adsorption and provide the desired gas sensor response time required of a gas measuring device.

The stannic oxide powder composition thus processed is prepared as a paste by using a convenient organic volatile liquid as a vehicle for the preparation of the paste. Typically this can be accomplished by disbursing the sintered stannic oxide powder mixture uniformly in $\beta$-terpineol.

The fabrication of the gas sensing device D of FIG. 2 is achieved by first applying film electrodes E, which may be typically gold paste, on an inert and non-conducting substrate S which may be typically alumina. Following the application of the spaced-apart electrodes E, a thick film of the stannic oxide sensor paste is applied, or painted, on a surface of the substrate S to effectively bridge the spaced-apart electrodes E. The thickness of the oxide film sensor SN is approximately 200 $\mu$m. Following the application of the spaced-apart electrodes E and the subsequent painting of the oxide paste SN, the combination of the substrate S, the electrodes E and the sensor SN is heated to approximately 400° C. for 1 hour. The electrode films E can be printed on the substrate S and pre-fired at temperatures approximately 800° C. for 10 minutes.

The degree of combustion of a fuel gas mixture G of FIG. 2 is related to the total concentration of the reducing gas, i.e., $H_2$, CO, etc., and the combustion product gases. More accurately it relates to the thermal chemical reduction potential in the combustion product. This reduction potential of the fuel gas mixture G is related to the amount of adsorbed oxygen on the surface of the semiconductor stannic oxide sensor SN that was removed by reaction with the reducing gases. This reaction is induced catalytically by the ingredients of the sensor SN when the sensor SN is heated to a predetermined temperature. The degree of removal of the adsorbed oxygen is monitored by the circuit C as a change in the electrical resistivity of the sensor SN. The preferred operating temperature of the sensor SN as an element in the gas measuring device D for the above-prepared stannic oxide film is in the range of between approximately 200° C. and 250° C. This temperature corresponds to the temperature at which the catalyst of the sensor composition is most effective to catalyze the surface reaction that produces the maximum change in electrical resistivity. This operating temperature can be achieved through the use of numerous heating techniques but a preferred technique is disclosed to be a film heater H secured to the substrate S and receiving excitation from a heater voltage source HV. The film heater H can be implemented through the use of resistance film compositions such as $NiCr_2O_4$ and $PbRuO_3$ which typically require electrical excitation in the range of approximately 1–2 volts to produce the desired temperature of between 200° and 250° C. The semiconductor stannic oxide film sensor SN is monitored by an EMF measuring circuit MC as a function of a change in voltage across the resistor R of the circuit C. The resistor R, is connected in series with a DC power supply PS, and exhibits an initial resistance value which can be preset to a predetermined level in the absence of a fuel reducing gas mixture G. On exposing the sensor SN of the gas measuring device D to a reducing gas mixture, the changes in the voltage as measured by the EMF measuring circuit MC are indicative of the fuel reducing constituents of the gas mixture G.

Figure 3:
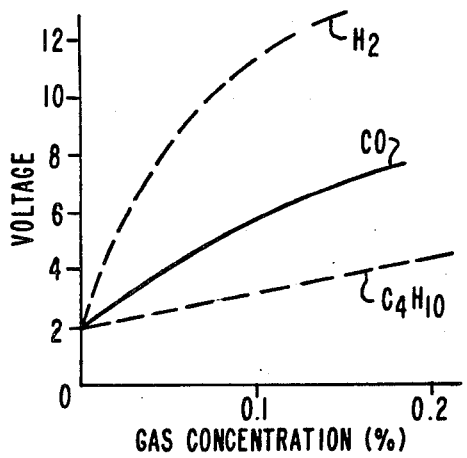

The proportionality between electrical resistivity decrease and reduction potential of a fuel-type gas such as $H_2$, CO, etc. is illustrated in FIG. 3. FIG. 3 illustrates the measured voltage across the resistor R as a function of gas concentration at about 200° C. and an applied voltage of 22 volts dc from the power source PS. Under certain conditions, the response of the device D will be selective by orders of magnitude towards one fuel constituent in the fuel gas mixture G. The graphical illustration in FIG. 3 shows data where the film detector SN is more sensitive towards $H_2$. Under conditions where the influence of adsorbed water vapor on the semiconductor oxide film detector SN is minimized, the device D becomes more sensitive towards CO. The addition of approximately 5 wt.% $ThO_2$ and 5 wt.% hydrophobic $SiO_2$ powders to the stannic oxide powder composition during the above processing produces a semiconductor oxide film which is selectively responsive to CO. While $ThO_2$ has been shown to be an attractive ingredient for trapping water away from the stannic oxide, thus rendering the film detector sensitive to CO, it has been determined experimentally that the substitution of a rare earth oxide for $ThO_2$ improves the adsorption of water vapor thus increasing the sensitivity of the semiconductor oxide film to CO. In particular, lanthanum oxide ($La_2O_3$) has been shown to be more hydroscopic than $ThO_2$ and when added to the semiconductor oxide powder in amount of approximately 5% in place of the combination of $ThO_2$ and $SiO_2$ it will enhance the sensitivity of the semiconductor oxide film to CO.

FIG. 4 illustrates the thick film device detection voltage versus oxygen/hydrogen ratio at 220° C. and 22 volts dc for a specific film composition. FIG. 5 illustrates the thick film device detection voltage versus oxygen/carbon monoxide ratio at 220° and 22 volts dc for a specific film composition.

While the above discussion of the semiconductor oxide film for use in a detector responsive to fuel constituents $H_2$ and CO has been directed to the use of stannic oxide, it has been determined experimentally that doped oxides, and in particular tin-doped indium sesquioxide when used in combination with the above-identified catalyst and sintering agent produces a film detector exhibiting operational stability at temperatures in excess of 250° C. Thus, this semiconductor oxide film detector can directly withstand the operating environments of processes exhibiting temperatures in the range of about 200° C. to 350° C. with the indium oxide exhibiting good electronic conductivity.

The simple construction of the above film sensors, and the packaging of the film sensors with battery power packs produces a much needed gas measuring device for providing control information in fuel-oxygen industrial processes.

We claim:

1. A method of preparing a stannic oxide gas detecting film device responsive primarily to $H_2$ present in an oxygen containing gas environment, comprising the steps of, solution precipitation of $Sn(SO_4)_2$ and $SnO_2$,
thermally decomposing the $Sn(SO_4)_2$ to $SnO_2$,
adding the $SnO_2$ to a catalyst solution of acetone or ethanol,
adding a sintering agent to the catalyst solution containing $SnO_2$ and stirring,
filtering the resulting catalyst dopeed oxide mixture,
drying the filtered mixture to produce a dry powder,
mixing the resulting dry powder with $\beta$-terpineol to form a paste,
applying the paste to a non-conductive substrate, and
drying the paste to form a stannic oxide gas detecting film.

2. A method as claimed in claim 1 wherein said step of thermally decomposing occurs at about 400° C.,
said step of drying the filtered mixture occurs at about 700° C. in about one hour, and
said step of drying the paste occurs at about 400° in about one hour.

3. A method of preparing a stannic oxide gas detecting film device responsive primarily to CO present in an oxygen containing gas environment, comprising the steps of, solution precipitation of $Sn(SO_4)_2$ and $SnO_2$,
thermally decomposing the $Sn(SO_4)_2$ to $SnO_2$,
adding the $SnO_2$ to a catalyst solution of acetone or ethanol,
adding a sintering agent to the catalyst solution containing $SnO_2$ and stirring,
filtering the resulting catalyst doped oxide mixture,
drying the filtered mixture to produce a dry powder,
adding $La_2O_3$ to the dried powder,
sintering the mixture of the $La_2O_3$ and the dry powder;
mixing the sintered mixture of $La_2O_3$ and dry powder with $\beta$-terpineol to form a paste,
applying the paste to a non-conductive substrate, and
drying the paste to form a stannic oxide gas detecting film.

4. A method as claimed in claim 3 wherein said step of thermally decomposing occurs at about 400° C.,
said step of drying the filtered mixture occurs at about 700° C. in about one hour, and
said step of drying the paste occurs at about 400° C. in about one hour.

* * * * *